US006638067B2

(12) United States Patent
Fischer et al.

(10) Patent No.: US 6,638,067 B2
(45) Date of Patent: Oct. 28, 2003

(54) FLOCKED ENDODONTIC FILES AND OTHER FLOCKED DEVICES

(75) Inventors: Dan E. Fischer, Sandy, UT (US); Bruce S. McLean, Sandy, UT (US)

(73) Assignee: Ultradent Products, Inc., South Jordan, UT (US)

( * ) Notice: Subject to any disclaimer, the term of this patent is extended or adjusted under 35 U.S.C. 154(b) by 13 days.

(21) Appl. No.: 09/946,128

(22) Filed: Sep. 4, 2001

(65) Prior Publication Data

US 2003/0044752 A1 Mar. 6, 2003

(51) Int. Cl.[7] .................. A61C 5/02
(52) U.S. Cl. .................. 433/102
(58) Field of Search .................. 433/102, 224

(56) References Cited

U.S. PATENT DOCUMENTS

| | | | | | |
|---|---|---|---|---|---|
| 717,594 | A | * | 1/1903 | Miles, Jr. | 433/102 |
| 5,236,358 | A | | 8/1993 | Sieffert | 433/119 |
| 5,337,436 | A | | 8/1994 | Saxer et al. | 15/104.94 |
| 5,378,149 | A | | 1/1995 | Stropko | 433/80 |
| 5,693,360 | A | | 12/1997 | Stern et al. | 427/2.29 |
| 5,800,367 | A | | 9/1998 | Saxer et al. | 601/164 |
| 5,816,804 | A | | 10/1998 | Fischer | 433/90 |
| 5,899,693 | A | | 5/1999 | Himeno et al. | 433/119 |
| 5,944,519 | A | | 8/1999 | Griffiths | 433/80 |
| 6,049,934 | A | | 4/2000 | Discko | 15/106 |
| 6,059,570 | A | | 5/2000 | Dragan et al. | 433/80 |
| 6,082,999 | A | | 7/2000 | Tcherny et al. | 433/80 |
| 6,083,002 | A | | 7/2000 | Martin et al. | 433/90 |
| 6,096,382 | A | | 8/2000 | Gueret | 427/463 |
| 6,179,617 | B1 | | 1/2001 | Ruddle | 433/224 |
| 2002/0172922 | A1 | | 11/2002 | Mannschedel | 433/102 |

FOREIGN PATENT DOCUMENTS

| | | |
|---|---|---|
| EP | 1 147 746 | 10/2001 |
| EP | 1 258 227 | 11/2002 |
| WO | WO 02/058761 | 8/2002 |
| WO | WO 02/053053 | 11/2002 |

OTHER PUBLICATIONS

Borowski, Bob, "Get a Feel for Flocking," pp. 1–4, Reprinted from *Screen Printing,* Mar. 1998.
Maag, Ulrich, "Principles of Flocking," pp. 1–6, reprinted from *Adhesives Age,* Sep. 1975, vol. 18, No. 9.

* cited by examiner

*Primary Examiner*—John J. Wilson
(74) *Attorney, Agent, or Firm*—Workman, Nydegger

(57) ABSTRACT

The invention generally provides flocked files for debriding root canals during endodontic procedures. The flocked files comprise a shank with a periphery surface and fibers that are flocked or otherwise attached to the periphery surface. The periphery surface comprises at least one flocked surface segment over which the fibers are dispersed and may include at least one abrading surface segment that is suitable for abrading or scraping the walls of the root canal. The fibers may be composed of various materials and may comprise various textures, Deniers, lengths, and flexibility. The fibers abrade and loosen potential irritants in the root canal architecture, including the recessed regions and the accessory canals, without requiring unnecessary reshaping and removal of dentin from the root canal. The fibers also capture and carry loosened debris out from the root canal.

25 Claims, 5 Drawing Sheets

FLOCKED ENDODONTIC FILES AND OTHER FLOCKED DEVICES

BACKGROUND OF THE INVENTION

1. The Field of the Invention

The present invention relates to the field of dental instruments. In particular, the present invention relates to endodontic files that are used for debriding and cleaning root canals during endodontic procedures. Even more particularly, the present invention relates to flocked endodontic files that are used to remove pulp, necrotic tissue, organic debris, and other potential irritants from root canals in preparation for receiving dental filling materials.

2. The Prior State of the Art

Endodontics is the branch of dentistry that generally deals with infections and diseases of dental pulp. Dental pulp, which is found in the pulp chamber and root canals of the tooth, comprises a vascular tissue that is generally composed of nerve fibers and blood vessels that nourish the tooth during its growth and development. When bacteria gains access to the pulp, either through a fractured tooth or a deep cavity, the pulp becomes infected and will die unless the body is able to repair and heal the pulp. Pulp can also become infected when the tooth suffers from trauma or a periodontal disease.

When the pulp becomes so severely infected or otherwise damaged that it cannot be healed, it is necessary to remove the pulp to relieve the pain and to prevent infection from spreading beyond the tooth. Pulp can either be removed by extracting the tooth or by performing an endodontic procedure, such as a root canal.

During a root canal procedure, the endodontist accesses the root canal and debrides the root canal of potential irritants such as necrotic tissue, pulp, bacteria, bacterial byproducts and other debris. Debridement essentially consists of loosening the potential irritants from the sides of the root canal with an endodontic tool, such as a file, and then flushing the potential irritants out of the root canal with an irrigant. Some irrigants may comprise or are used in combination with antibacterial disinfectants and/or chelators to sanitize the root canal and to dissolve remaining debris.

The final step of performing the root canal procedure, which is known as obturation, involves filling the root canal with a filling material such as gutta percha or amalgam and sealing the filling with a sealer cement to prevent future contamination of the root canal.

One problem with existing methods and devices for performing endodontic procedures, however, is that the anatomy of the tooth makes it difficult to completely clean potential irritants out of the root canal. In particular, the root canal is irregularly shaped, having contoured surfaces, recessed regions and accessory canals. The irregular shape of the root canal prevents existing endodontic files from reaching and abrading the entire surface area of the root canal, thereby leaving portions of live diseased or necrotic pulp and debris undisturbed.

Some existing flexible endodontic files are capable of following the irregular contours of the perimeter surfaces of the root canal. However, even these existing flexible files are unable to completely reach and abrade the recessed regions and accessory canals of the root canal. Accordingly, to provide access to the hard-to-reach regions of the root canal, it is often necessary to "reshape" or file down the walls of the root canal. This however, is undesirable because it can cause overthinning of the root canal which increases the risk that an endodontic tool, such as a file or an irrigation cannula, will fracture or perforate the walls of the root canal, causing pain to the patient and further complicating the endodontic procedure.

Reshaping is sometimes required to widen narrow passages of the root canal in order to access apical regions and to minimize hydraulic pressures during obturation. However, filing down the walls of the root canal unnecessarily, simply to provide access to recessed regions for debridement is undesirable, not only because it increases the risks associated with overthinning, but also because it increases the time, and hence the cost, associated with performing the root canal. Furthermore, even after reshaping the root canal, existing endodontic files are still sometimes unable to adequately reach and abrade the recessed regions and accessory canals.

Accordingly, there is currently a need in the art for improved endodontic files for debriding root canals during endodontic procedures.

SUMMARY OF THE INVENTION

The present invention is directed to improved endodontic files used to debride root canals during endodontic procedures. The improved endodontic files of the invention comprise flocked files for abrading and removing pulp, necrotic tissue, organic debris, and other potential irritants from the root canal structures, including the recessed regions and the accessory canals.

Each of the flocked files of the invention comprises a shank with a periphery surface, and fibers that are flocked or otherwise attached to the periphery surface. In one preferred embodiment, the periphery surface comprises at least one abrading surface segment with edges that are suitable for abrading or filing the walls of the root canal and at least one flocked surface segment over which multiple fibers are dispersed.

The edges of the abrading surface can be formed in any suitable manner, such as, for example, by machining the periphery surface, by twisting the shank, or by depositing abrasive materials such as diamond, ceramic, and metallic particles on the periphery surface. When the edges of the abrading surface are scraped against the walls of the root canal the potential irritants on the walls are loosened. With sufficient scraping by the abrading surface, the walls of the root canal can also be reshaped or filed down.

The flocked surface segment of the flocked file comprises multiple fibers that are also useful for scrubbing and abrading the root canal surfaces. The flocked surface segment may be separated from or overlap the abrading surface segment and may comprise a single continuous flocked surface segment or multiple separated flocked surface segments.

The fibers disposed on the flocked surface segment(s) assist in the debridement of the root canal and are particularly useful for reaching and abrading the hard-to-reach areas, such as the recessed regions and the accessory canals, without requiring unnecessary reshaping and removal of dentin from the root canal. The fibers may be composed of various plastics, metals or any combination thereof. Suitable plastics include, but are not limited to, polypropylene, polyethylene, nylon and polyester. Suitable metals include, but are not limited to, tungsten and titanium.

The fibers may comprise a uniform length or varying lengths with a preferred length within the range from about 0.3 mm to about 3 mm, and more preferably within a range from about 0.7 mm to about 1.5 mm. The diameters of the fibers may also vary, preferably within a range from about 1 Denier to about 15 Denier, and more preferably within a range from about 1.5 Denier to about 10 Denier. It will be appreciated that the length and diameter of the fibers, as well as the texture, flexibility and the density of distribution of the fibers may vary to accommodate different needs and preferences.

The fibers can be attached to the flocked surface segment by any suitable process, such as electrostatic flocking, injection molding, and welding. In one preferred embodiment, the fibers are electrostatically flocked onto the flocked file segment and secured by an adhesive. The adhesive in the preferred embodiment is a flexible and water insoluble adhesive, such as a polyurethane or flexible acrylic adhesive. Flexible adhesives are particularly useful when the fibers are stiff or rigid because it allows the fibers to bend at their points of affixation. It should be appreciated, however, that other adhesives such as epoxies and silicones can also be used.

In some embodiments, the flocked files of the invention also comprise a handle and a tip. The tip may be configured for scraping or cutting, or alternatively, the tip may be blunt. The handle is used to manipulate and move the flocked file within the root canal.

When the flocked file is rotated or moved up and down within the root canal, the fibers brush against and loosen the pulp, necrotic tissue, organic debris, and other potential irritants in the root canal. The fibers of the flocked file are able to loosen the potential irritants in the recessed regions and accessory canals more effectively than existing prior art endodontic files, without requiring unnecessary reshaping of the root canal. The fibers are also useful for carrying the loosened debris out from the root canal, for evenly distributing solutions, and for reducing hydraulic pressures by rupturing trapped air pockets.

In one alternative embodiment of the invention, the periphery surface does not include an abrasive surface segment. Rather, according to this alternative embodiment, the fibers provide the entire utility of abrading and loosening the pulp, necrotic tissue, organic debris, and other potential irritants in the root canal. In such an embodiment, rigid fibers are preferred. However, it should be appreciated that the flocked file may comprise any combination of rigid and flexible fibers.

One skilled in the art will appreciate that flocked files of the present invention are an improvement over the prior art for at least providing a means for reaching, abrading, and loosening the potential irritants in the root canal more effectively than existing files without requiring unnecessary reshaping and overthinning of the root canal. The flocked files of the invention are also an improvement over the prior art files for at least providing fibers to assist in the removal of the loosened debris from the root canal.

These and other benefits, features and advantages of the flocked files of the present invention will become more fully apparent from the following description and appended claims, or may be learned by practicing the invention as set forth below.

BRIEF DESCRIPTION OF THE DRAWINGS

A more extensive description of the present invention, including the above-recited features and advantages, will be rendered with reference to the specific embodiments that are illustrated in the appended drawings. Because these drawings depict only exemplary embodiments, the drawings should not be construed as imposing any limitation on the present invention's scope. As such, the present invention will be described and explained with additional specificity and detail through use of the accompanying drawings in which.

DETAILED DESCRIPTION OF THE PREFERRED EMBODIMENTS

The present invention relates to improved endodontic files used to debride root canals during endodontic procedures. More particularly, the present invention relates to flocked files for removing pulp, necrotic tissue, organic debris, and other potential irritants from root canals during endodontic procedures.

Figure 1:
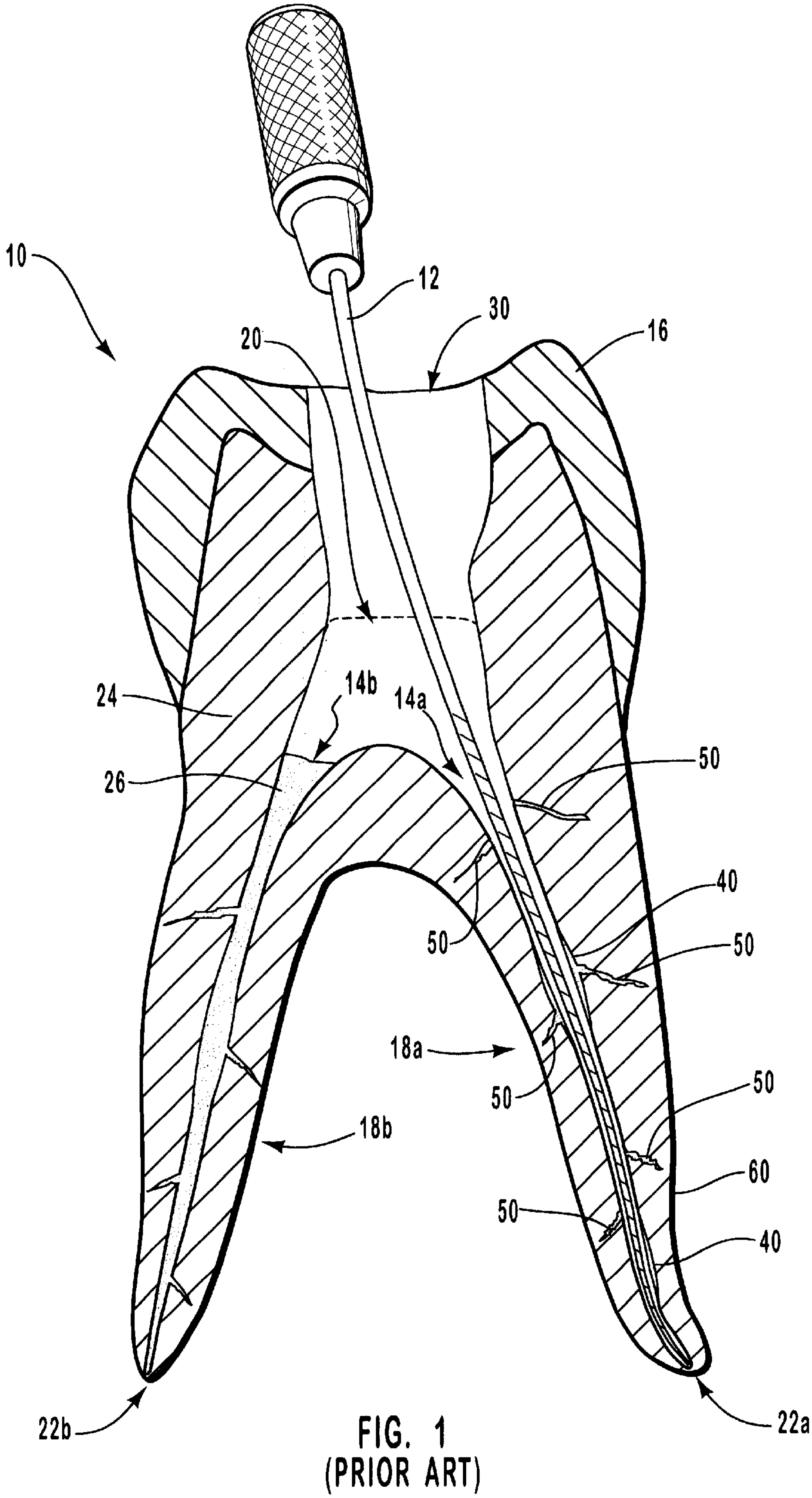
FIG. 1 illustrates a cross-sectional side view of a tooth with a prior art file inserted into the root canal of the tooth.

FIG. 1 illustrates a cross-sectional side view of a tooth 10 with an existing prior art file 12 inserted into a root canal **14*a* of the tooth 10. As shown, the tooth 10 comprises a crown 16 and two roots 14*a* and 14*b*. The crown 16 is made of enamel and is generally exposed to the inside of the mouth. The roots 18*a* and 18*b* are not exposed, but rather, they are embedded within the gingivae (e.g., gum tissue), which is not shown. The tooth 10 also comprises a pulp chamber 20, and two root canals 14*a* and 14*b*. Each of the root canals 14*a* and 14*b* extend from the pulp chamber 20 to an apex 22*a* and 22*b* where the root canals 14*a* and 14*b* are supplied by the mandibular canal (not shown). The tooth 10 also comprises dentin 24, a bone-like material that supports the enamel crown 16. Although tooth 10** is depicted as having two roots and two root canals, it should be appreciated that a tooth may comprise only a single root and a single corresponding root canal.

The pulp chamber 20 and each of the root canals 14*a* and 14*b* are typically filled with pulp 26. However, in FIG. 1 most of the pulp 26 has been removed as part of an endodontic procedure, which is described below. Pulp generally comprises vascular tissue composed of nerve fibers and blood vessels that are essential to the nourishment of the tooth 10 during its growth and development. When bacteria gains access to the pulp 26, the pulp 26 becomes infected and will die unless the body is able to repair and heal the pulp 26. When the pulp 26 becomes so severely infected or otherwise damaged that it cannot be healed, it is necessary to remove the pulp 26. One method for removing the pulp 26 is to perform the endodontic procedure commonly known as a root canal.

In performing the root canal procedure, such as on root canal 14*a*, the endodontist drills a hole 30 through the dentin 24 to access the pulp chamber 20 and the infected root canal 14*a*. The endodontist then uses an endodontic tool, such as file 12 to clean the pulp and other potential irritants out from the root canal 18. One problem with existing files, however, is that they are unable to adequately debride the root canal 14*a* of potential irritants. In particular, the root canal 14*a* comprises multiple recessed regions 40 and accessory canals 50 that line the root canal 14*a*. Each of these hard to reach areas may contain pulp, necrotic tissue, and other potential irritants that need to be removed, but cannot be reached by existing files. Accordingly, even after cleaning the root canal 18 with a file, potential irritants may still reside inside of the root canal 14*a*. Therefore, it is sometimes required to reshape or widen the root canal 14*a* to provide access to the recessed regions 40 and accessory canals 50. However, with reshaping there is a risk of overthinning the walls of the root 18*a*, thereby increasing the probability that an endondontic tool will puncture or rupture the cementum seal 60 encasing the root 18*a*, thereby causing pain to the patient and further complicating the endodontic procedure. Furthermore, even after reshaping the root canal 14*a*, some hard to reach areas may still be out of reach.

The flocked files of the present invention minimize the risks associated with reshaping the root canal 14*a* by providing flocked fibers that are able to reach and abrade the recessed regions 40 and accessory canals 50 more effectively than is currently possible with the prior art files, without requiring unnecessary reshaping and overthinning of the root canal 14*a*.

Figure 2:
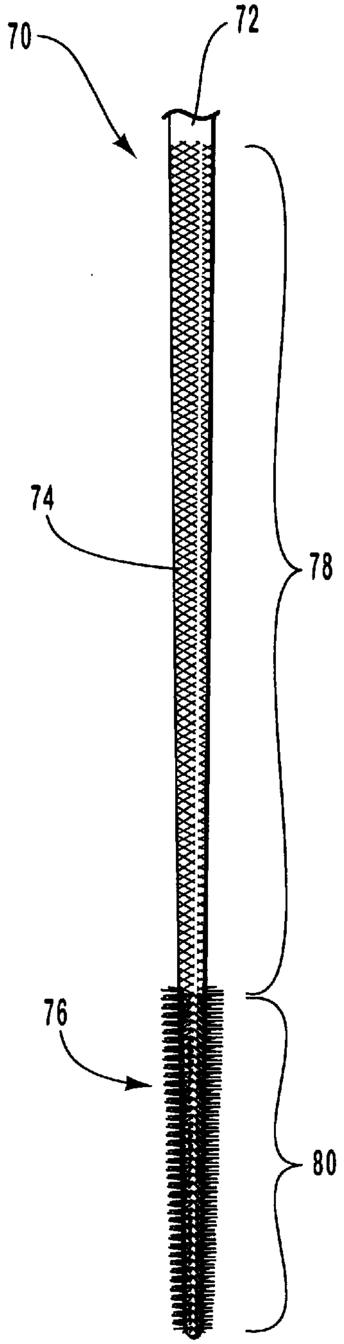
FIG. 2 illustrates one embodiment of the flocked file of the present invention in which the flocked file comprises a cylindrical shank and a periphery surface that includes a flocked surface segment having multiple fibers disposed thereon and an abrasive surface segment that is formed by machining the shank.

FIG. 2 shows one embodiment of a flocked file 70 of the invention. As shown, the flocked file 70 comprises a shank 72 that includes a periphery surface 74 and multiple fibers 76 that are flocked or otherwise attached to the periphery surface 74. The periphery surface 74 comprises at least one abrading surface segment 78 with edges that are suitable for abrading or scraping the walls of the root canal and at least one flocked surface segment 80 over which the multiple fibers 76 are disposed. When the edges of the abrading surface segment 78 are scraped against the walls of the root canal the potential irritants on the walls of the root canal are loosened and/or dislodged so that they can be removed by irrigation or carried out on the multiple fibers 76. The abrading surface segment 78 is also useful for reshaping the root canal when required. For instance, with sufficient scraping by the edges of the abrading surface segment 78, the walls of the root canal can be filed down to a desired shape.

According to one present embodiment, the edges of the abrading surface segment 78 are formed by machining or forging grooves into the periphery surface 74. It should be appreciated, however, that the edges can also be formed by other suitable processes. For example, the edges of the abrading surface segment can also be formed by twisting an angular blank, such as a rectangular blank or a triangular blank until the edges are twisted into a desired configuration that is suitable for scraping against the surfaces of the root canal. The flocked file shown in FIG. 3, illustrates such an embodiment in which the edges of the abrading surface segment 78 are formed by twisting rectangular blank 82.

Figure 4:
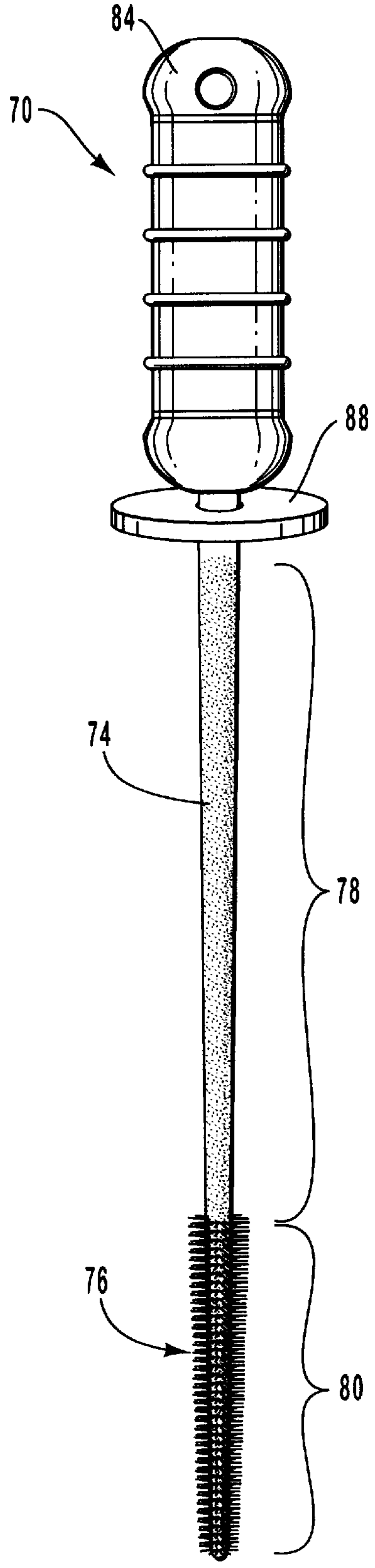
FIG. 4 illustrates one embodiment of the flocked file of the present invention in which the flocked file comprises a cylindrical shank, a handle, a stop, and a periphery surface that includes a flocked surface segment having multiple fibers disposed thereon and an abrasive surface segment that is formed by depositing an abrasive material on the periphery surface.

In another embodiment, shown in FIG. 4, the edges of the abrading surface segment 78 of the periphery surface 74 may comprise the edges of an abrasive material that is deposited on the abrasive surface segment 78. Suitable abrasive materials include, but are not limited to, diamond, ceramic, and metallic particles and powders. The abrasive material may be secured to the abrading surface segment 78 with any suitable adhesive, such as epoxy, or with any suitable process, such as welding.

Figure 3:
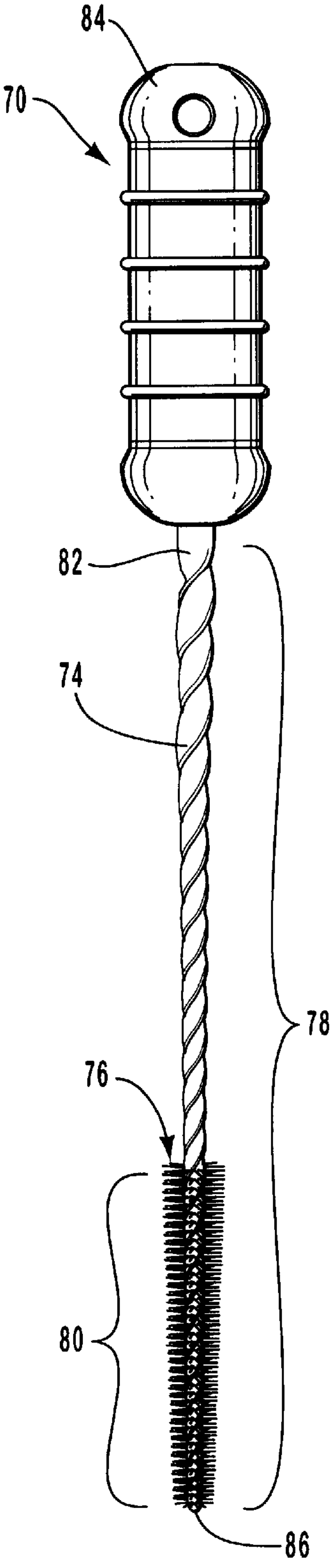
FIG. 3 illustrates one embodiment of the flocked file of the present invention in which the flocked file comprises an angular shank, a handle, and a periphery surface that includes a flocked surface segment having multiple fibers disposed thereon and an abrasive surface segment that is formed by twisting the shank.

As shown in FIGS. 2–4, the flocked files of the invention comprise a flocked file segment 80 over which multiple fibers 76 are disposed. The multiple fibers 76 are particularly useful for brushing and abrading the hard to reach areas of the root canal, such as the recessed regions and accessory canals, that cannot be reached by the abrading surface segment 78. The fibers 76 are also useful for applying solutions, such as irrigants, to the root canal. In particular, the fibers 76 can brush the solutions onto the surfaces of the root canal while at the same time disrupting the formation of air bubbles and air pockets. It will be appreciated that this minimizes the hydraulic pressures that are created when the solution is introduced into the root canal while at the same time enabling the solution to be evenly distributed over the entire surface area of the root canal. It will be appreciated that some irrigants may comprise or are used in combination with antibacterial disinfectants and/or chelators to sanitize the root canal and to dissolve remaining debris, such as compositions that include sodium hypochlorite.

The fibers 76 may be composed of various plastics, metals or any combination thereof. Suitable plastics include, but not limited to, polypropylene, polyethylene, nylon and polyester. Suitable metals include, but not limited to, tungsten and titanium. The fibers 76 may also comprise various cut lengths, which may be uniform or vary. According to one preferred embodiment, the cut length of the fibers 76 is within the range from about 0.3 mm to about 3 mm, and more preferably within a range from about 0.7 mm to about 1.5 mm. The diameters of the fibers 76 may also vary, preferably within a range from about 1 Denier to about 15 Denier, and more preferably within a range from about 1.5 Denier to about 10 Denier. The texture, flexibility and the density of distribution of the fibers 76 on the flocked surface segment 80 may also vary to accommodate different needs and preferences.

The fibers 76 can be attached to the flocked surface segment 80 by any suitable process, such as electrostatic flocking, injection molding, and welding. In one preferred embodiment, the fibers are electrostatically flocked onto the flocked file segment 80 and secured by an adhesive. The adhesive in the preferred embodiment is a flexible and water insoluble adhesive, such as a polyurethane or flexible acrylic adhesive. Flexible adhesives are particularly useful when the fibers are stiff or rigid because it allows the fibers to bend at the point of affixation. It should be appreciated, however, that other adhesives such as epoxies and silicones may also be used, and the adhesives may comprise various physical properties to accommodate different needs and preferences.

As shown in FIG. 3, the flocked files of the invention may also comprise a handle 84 and a tip 86. The tip 86 may be configured for scraping or cutting, or alternatively, the tip 86 may be blunt, as shown. The handle 84 is used to manipulate and move the flocked file 70 within the root canal. When a handle 84 is included, it may also be desirable to use a hand piece for facilitating movement of the flocked file 70, such as the hand piece disclosed in U.S. patent application Ser. No. 09/425,849, entitled "Systems for Incrementally Adjusting the Working Length of Endodontic Instruments" and U.S. patent application Ser. No. 09/425,857, entitled "Incrementally Adjustable Endodontic Instruments," both of which were filed on Oct. 22, 1999 and are incorporated herein by reference. It will be appreciated, however, that it is not necessary that the flocked files of the invention comprise a handle, as illustrated by FIG. 2. Without a handle, it is still possible to manipulate and move the flocked file 70 within the root canal by holding the shank 72 with fingers, pliers, or another tool.

As shown in FIG. 4, the flocked files of the invention may also comprise a stop 88 to abut against the crown of the tooth and to keep the tip of the flocked file 70 from penetrating too far into the root canal and for working on only predetermined portions of the root canal at a time. U.S. patent application Ser. No. 09/536,821, entitled "Endodontic Systems and Methods for the Anatomical Sectional and Progressive Corono-Apical Preparation of Root Canals With Instruments Using Stops," filed Mar. 27, 2000, and which is incorporated herein by reference, describes various other endodontic files with stops that can be combined with the teachings of the present invention.

Figure 5:
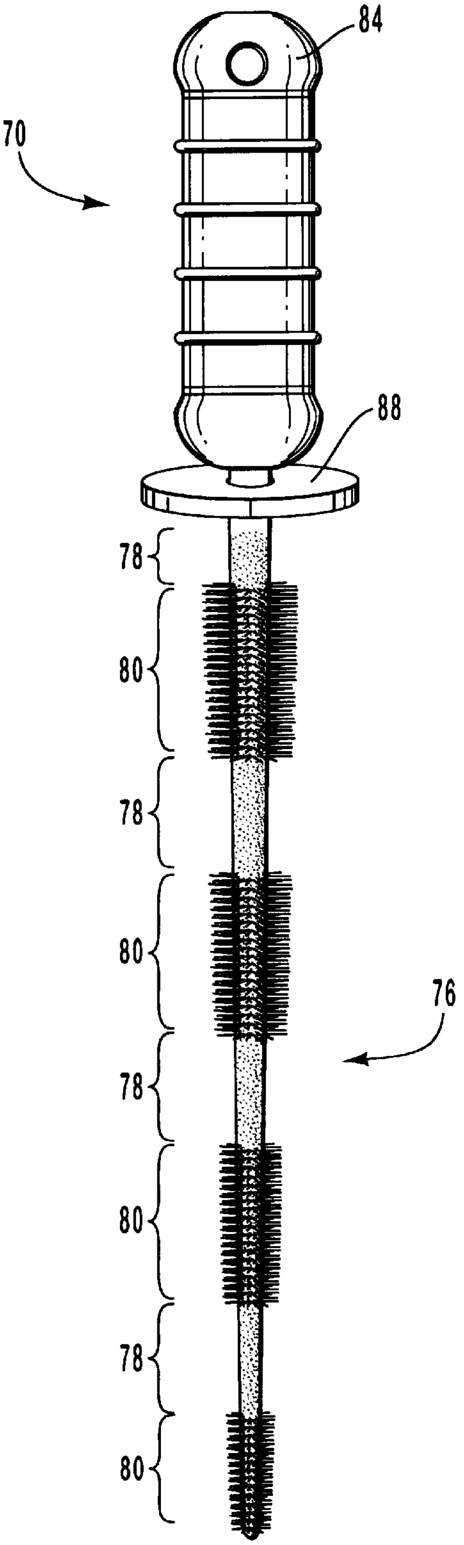
FIG. 5 illustrates one embodiment of the flocked file of the present invention in which the flocked file comprises a cylindrical shank, a handle, a stop, and a periphery surface that includes multiple flocked surface segments having multiple fibers disposed thereon and multiple abrasive surface segments separating the multiple flocked surface segments.

FIG. 5 illustrates another embodiment of the flocked file of the invention. In this embodiment, the flocked file 70 comprises multiple flocked surface segments 80 and multiple abrading surface segments 78. This embodiment is particularly useful for simultaneously brushing and abrading multiple areas of the root canal while providing areas along the flocked file 70 for capturing and retaining dislodged debris, as will be shown and described in reference to FIG. 6.

Figure 6:
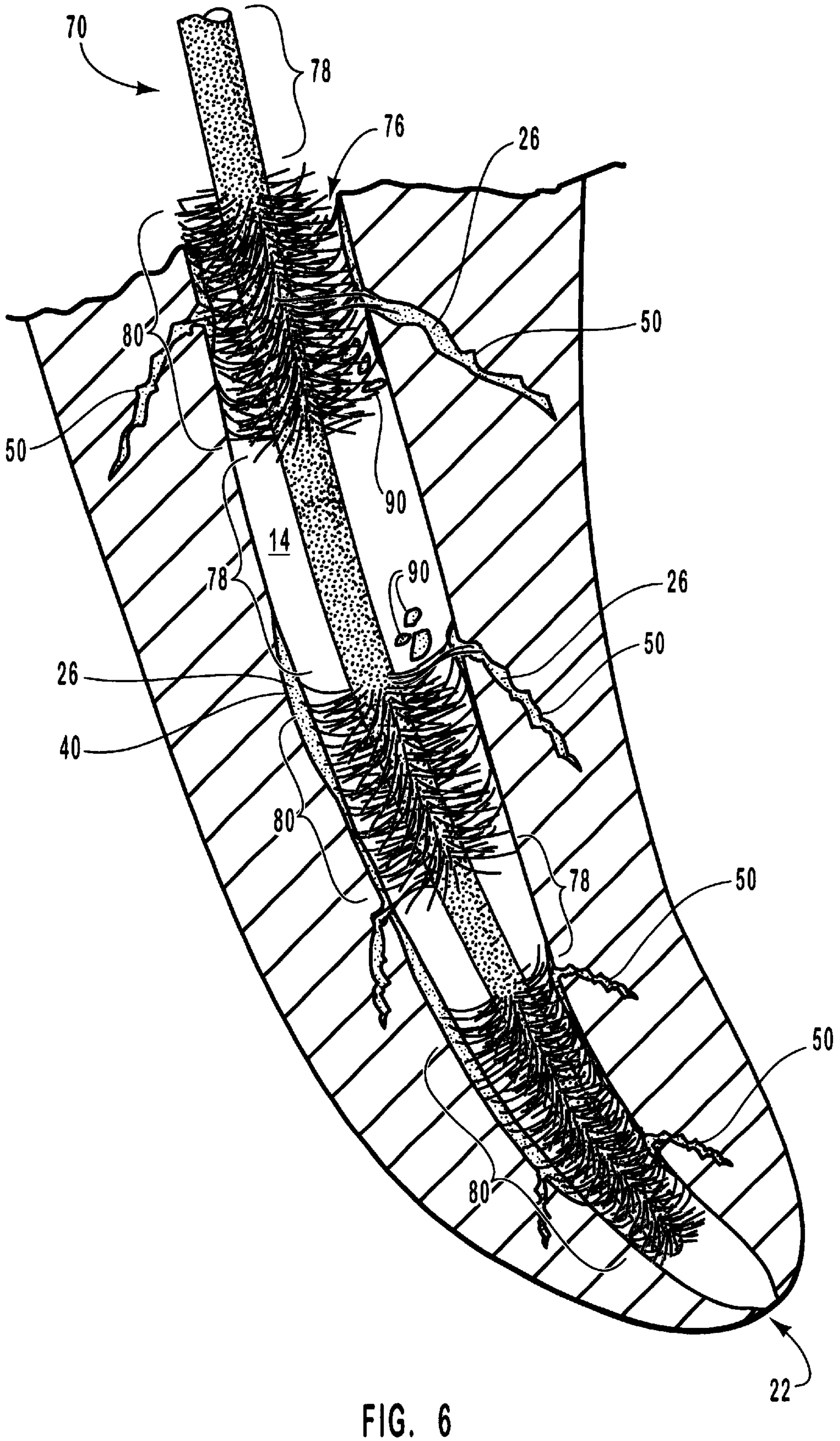
FIG. 6 illustrates a cross-sectional side view of a tooth with a flocked file of FIG. 5 inserted within the root canal of the tooth.

FIG. 6 illustrates the flocked file 70 of FIG. 5 inserted within a root canal 14. As shown, the flocked file 70 comprises multiple flocked surface segments 80 and multiple abrading surface segments 78. The abrading surface segments 78 can abrade the majority of the root canal 14 when they are manipulated against the surfaces of the root canal. However, the abrading surface segments 78, cannot reach and abrade the pulp and other potential irritants that are located within the recessed regions 40 and accessory canals 50. It will be appreciated that this is the same problem faced by existing files. To overcome this problem, the flocked files of the invention provide fibers 76 that are able to reach and abrade the surfaces of the root canal 14, even in the recessed regions 40, as shown in FIG. 6.

The fibers 76 are also able to extend into the accessory canals 50 when the flocked surface segments 80 are manipulated against the surfaces of the root canal 14. Accordingly, by rotating and moving the flocked file up and down within the root canal, the flocked files of the invention are able to clean the root canal 14 of potential irritants more effectively than is possible with existing endodontic files, and without requiring unnecessary reshaping and overthinning of the root canal 14. If reshaping of the root canal is required, however, the flocked file 70 of the present embodiment can be firmly pressed against the surfaces of the root canal. This will cause the fibers 76 to bend and will allow the edges of the abrading surface 78 to scrape against and reshape the surfaces of the root canal 14.

Another benefit of the present embodiment is for facilitating the removal of potential irritants from the root canal. In particular, the profiles of the abrading surface segments 78 are recessed from the fibers 76 and are suitable for receiving dislodged debris 90 so that it can be pushed up and out of the root canal 14 by the fibers 76. The fibers 76 also facilitate the removal of debris 90 by capturing and holding the debris 90 between the fibers 76 until it is pulled out of the root canal 14.

Yet another benefit of the flocked files of the invention is that the fibers 76 urge the flocked files towards the center of the root canal 14. This is a benefit because it minimizes the risk of 'ledging.' Ledging occurs when a practitioner attempts to insert an endodontic tool down to the apex 22 of the root canal 14 and the tip of the endodontic tool is halted prematurely against the sidewall of the root canal 14. The downward pressure exerted on the tool can cause the tip to dig into the side of the root canal and form a ledge. Such ledges are difficult to bypass, and if the ledge occurs very close to the apex 22, the ledge may give the practitioner the mistaken impression that the apex 22 has been reached.

Figure 7:
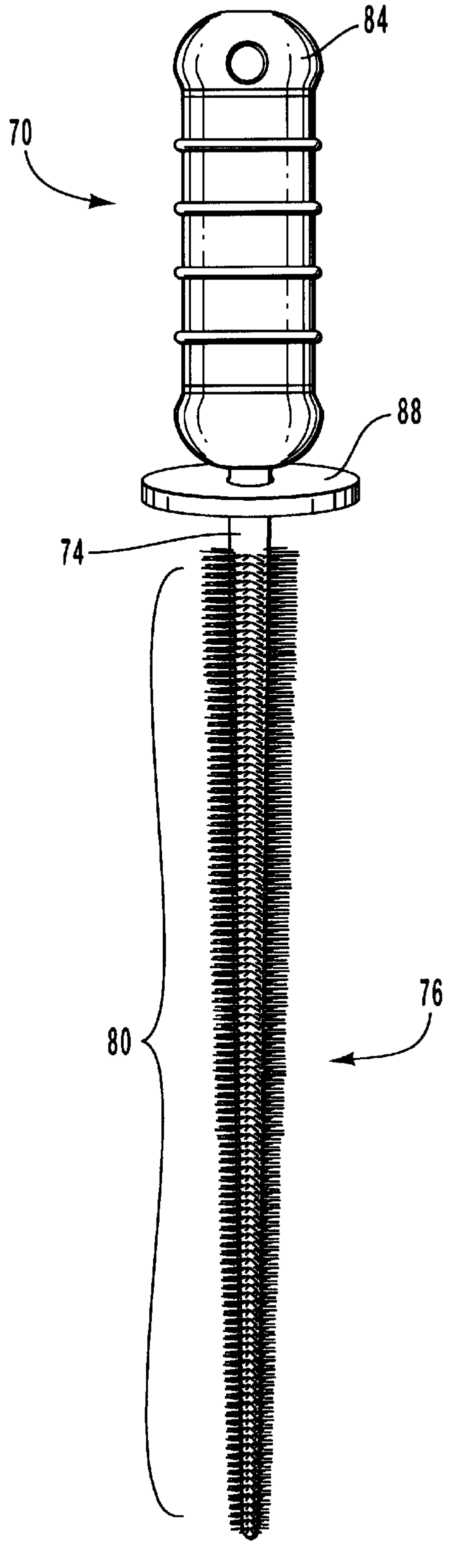
FIG. 7 illustrates one embodiment of the flocked file of the present invention in which the flocked file comprises a shank, a handle, a tip, and a periphery surface that includes a flocked surface segment extending substantially from the tip to the handle with multiple fibers disposed thereon.

Turning now to FIG. 7, one alternative embodiment of the invention is shown. In this embodiment, the periphery surface 74 does not include an abrasive surface segment. Rather, according to this alternative embodiment, the periphery surface 74 only includes a flocked fiber segment 80 with fibers 76 that are configured to be abrasive enough that they alone provide the entire utility of abrading and loosening the pulp, necrotic tissue, organic debris, and other potential irritants in the root canal. In such an embodiment, rigid fibers are preferred. However, it should be appreciated that the flocked file 70 may also comprise any combination of rigid and flexible fibers 76.

Figure 8:
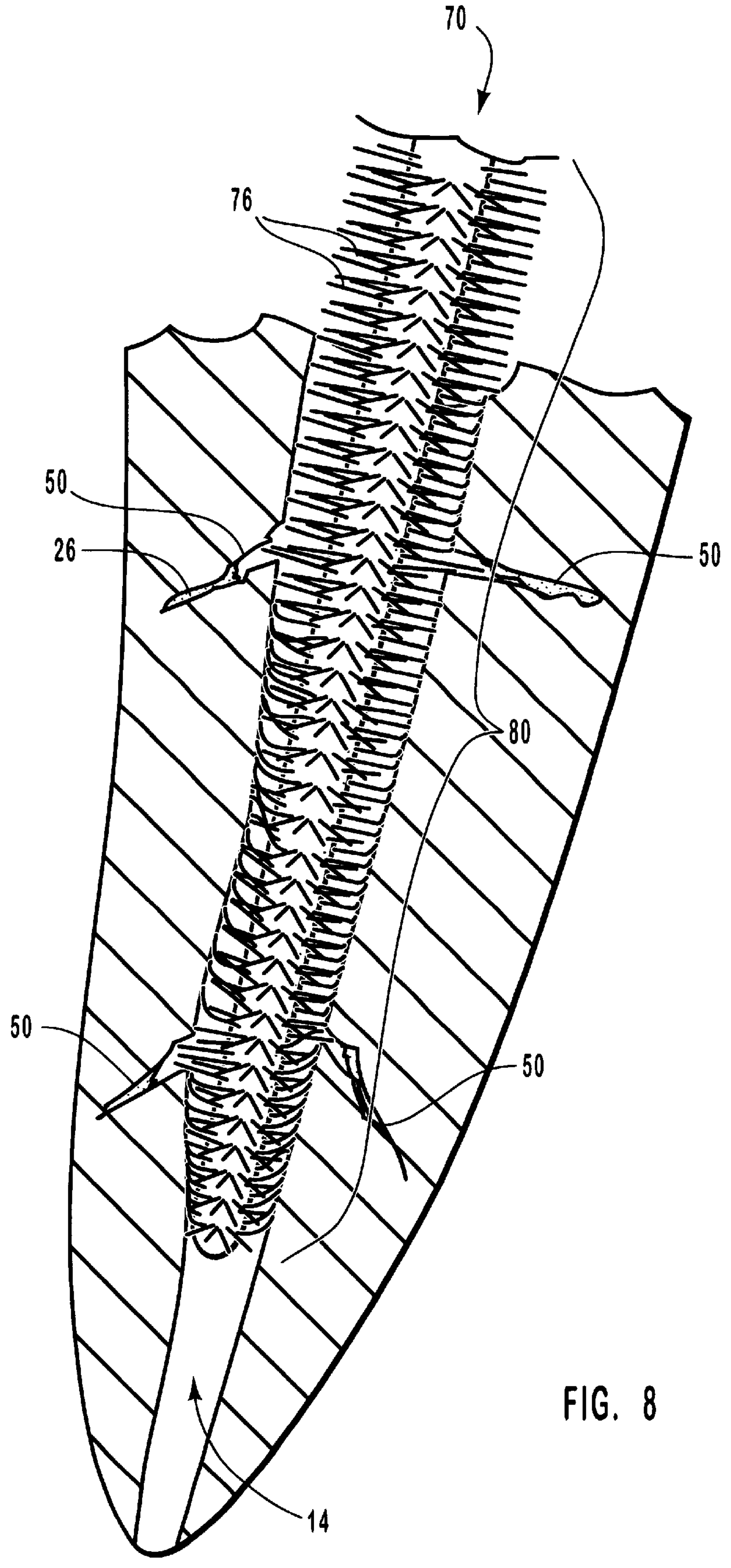
FIG. 8 illustrates a cross-sectional side view of a tooth with a flocked file of FIG. 7 inserted within the root canal of the tooth.

FIG. 8 illustrates one implementation of the flocked file of FIG. 7. As shown, the fibers 76 are distributed over the entire flocked file segment 80 and the flocked file 70 is inserted within the root canal 14. According to this embodiment, the fibers 76 of the flocked file 70 comprise both very short rigid fibers composed of a metal, such as titanium, and longer more flexible fibers composed of a plastic, such as nylon.

The short rigid fibers provide a suitable abrasive for scraping and debriding the easy to reach areas of the root canal 14 and when required, they can also be used to reshape and file down the surfaces of the root canal 14. In some circumstances it is desirable that the short rigid fibers are somewhat flexible so that they can move in and around the irregularities of the root canal 14. In these circumstances the short rigid fibers are affixed to the flocked file 70 with a flexible adhesive that allows the short rigid fibers to bend at their points of affixation without eliminating the abrasive quality of the fibers. The longer more flexible fibers are long enough and flexible enough to reach and abrade the hard to reach areas of the root canal, such as the accessory canals 50.

Accordingly, one skilled in the art should appreciate that flocked files of the present invention are an improvement over the prior art for at least providing a means for reaching, abrading, and removing the potential irritants from the root canal without requiring unnecessary reshaping and overthinning of the root canal. The flocked files of the invention are also beneficial for minimizing the risks of ledging and for facilitating the application of solutions to the root canal while minimizing hydraulic pressures created by trapped air pockets.

Although specific detail has been provided regarding various embodiments of the flocked files of the invention, it should be appreciated that the present invention may be embodied in other forms without departing from its spirit or essential characteristics. For example, it should be appreciated that the fibers disposed on the flocked files of the invention may comprise various compositions, lengths, textures, flexibilities, diameters, and densities of distributions. The fibers may also be disposed in any desired configuration on the flocked file, whether evenly, unevenly, or in patterns. The abrading surface segments and the flocked surface segments may also be configured in any desired configuration. For example, as shown in FIG. 3, the flocked surface segment 80 may overlap the abrading surface segment 78. Furthermore, there may also be portions of the periphery surface that comprises neither an abrading surface segment, nor a flocked surface segment.

Accordingly, as properly understood, the preceding description of specific embodiments is illustrative only and in no way restrictive. The scope of the invention is, therefore, indicated by the appended claims as follows.

What is claimed and desired to be secured by United States Letters Patent is:

1. An endodontic file for debriding a root canal comprising:

a shank having a periphery surface extending over the shank;

at least one abrading surface segment that is disposed on the periphery surface and that is configured with edges that are suitable for scraping and filing surfaces of the root canal; and at least one flocked surface segment that is disposed on the periphery surface comprising multiple fibers that are somewhat flexible and configured for scrubbing recessed regions and accessory canals of the root canal.

2. An endodontic file as defined in claim 1, wherein the multiple fibers are composed of at least one of nylon, polyester, polypropylene, polyethylene, acrylic, tungsten, and titanium.

3. An endodontic file as defined in claim 2, wherein the multiple fibers are attached to the periphery surface with a water insoluble adhesive.

4. An endodontic file as defined in claim 2, wherein the multiple fibers are attached to the periphery surface by electrostatic flocking.

5. An endodontic file as defined in claim 1, wherein the at least one flocked surface segment overlaps at least a portion of the at least one abrading surface segment.

6. An endodontic file as defined in claim 1, wherein the of the at least one abrading surface are configured to file down walls of the root canal to a desired shape.

7. An endodontic file as defined in claim 1, wherein the shank is an angular shank, and wherein the edges of the at least one abrading surface are formed by twisting the shank.

8. An endodontic file as defined in claim 1, wherein the edges of the at least one abrading surface formed by machining the periphery surface.

9. An endodontic file as defined in claim 1, wherein the file further comprises a handle that is fixedly attached to the proximal end.

10. An endodontic file as defined in claim 9, wherein the file further comprises a tip located at the distal end, and wherein the flocked surface segment is located proximate the tip.

11. An endodontic file as defined in claim 1, wherein the at least one flocked surface segment overlaps at least a portion of the at least one abrading surface segment.

12. An endodontic file as defined in claim 1, wherein the file comprises multiple flocked surface segments, each of said multiple flocked surface segments being separated by portions of the at least one abrading surface segment.

13. An endodontic file as recited in claim 1, further comprising a stop configured to abut against a tooth surface to prevent the endodontic file from penetrating too far into the root canal.

14. An endodontic file comprising:

a flexible shank having a proximal end opposite a distal end, the shank tapering from the proximal end to the distal end;

a periphery surface extending from the proximal end to the distal end;

at least one flocked surface segment located on the periphery surface; and fibers disposed on the at least one flocked surface segment, said fibers comprising rigid fibers and flexible fiber, the flexible fibers being longer than the rigid fibers.

15. An endodontic file as defined in claim 14, wherein the fibers are composed of at least one of nylon, polyester, polypropylene, polyethylene, acrylic, tungsten, and titanium.

16. An endodontic file us defined in claim 14, wherein the fibers comprise lengths in the range of approximate 0.3 mm to approximately 3 mm.

17. An endodontic file as defined in claim 14, wherein the flocked surface segment covers the entire periphery surface.

18. An endodontic file for debriding a root canal, comprising:

a flexible shank having a periphery surface extending over the shank;

at least one abrading surface segment that is disposed on the periphery surface and that is configured with edges that are suitable for scraping and filing surfaces of the root canal; and multiple separated flocked surface segments that are disposed on the periphery surface of the shank, each of the flocked surface segments comprising multiple fibers are scrubbing the root canal, and each of the flocked surface segments being separated from other of the flocked surface segments by one or more portions or the at least one abrading surface segment.

19. An endodontic file as defined in claim 18, wherein at least one of the multiple flocked surface segments overlaps at least a portion of the at least one abrading surface segment.

20. An endodontic file as defined in claim 18, wherein said multiple fibers are composed of at least one of nylon, polyester, polypropylene, polyethylene, acrylic, tungsten, and titanium.

21. An endodontic file for debriding a root canal, comprising:

a shank having a periphery surface extending over the shank;

at least one abrading surface segment that is disposed on the periphery surface, comprising an abrasive material that is deposited on the periphery surface, the abrasive material being configured for scraping and filing surfaces of the root canal; and at least one flocked surface segment that is disposed on the periphery surface, comprising multiple fibers for scrubbing recessed regions and accessory canals of the root canal.

22. An endodontic file as recited in claim 21, wherein the abrasive material includes at least one of diamond particles ceramic particles and metallic particles.

23. An endodontic file as recited in claim 22, wherein the abrasive material includes at least one of diamond powder, ceramic powder and metallic particles.

24. An endodontic tile as recited in claim 21, wherein the abrasive material is secured to the abrading surface segment with an adhesive.

25. An endodontic file as recited in claim 21, wherein the abrasive material is secured to the abrading surface with a welding process.

* * * * *

UNITED STATES PATENT AND TRADEMARK OFFICE
CERTIFICATE OF CORRECTION

PATENT NO. : 6,638,067 B2
DATED : October 28, 2003
INVENTOR(S) : Fischer et al.

It is certified that error appears in the above-identified patent and that said Letters Patent is hereby corrected as shown below:

Column 1,
Line 58, after "live" please insert -- , --

Column 9,
Line 42, after "wherein the " please insert -- edges --

Column 10,
Line 10, please replace "fiber" with -- fibers --
Line 31, please replace "are" with -- for --
Line 34, please replace "or" with -- of --

Signed and Sealed this

Seventeenth Day of August, 2004

JON W. DUDAS
*Acting Director of the United States Patent and Trademark Office*